(12) United States Patent
Troisi et al.

(10) Patent No.: US 9,192,594 B2
(45) Date of Patent: Nov. 24, 2015

(54) OPHTHALMIC SOLUTION FOR PROTECTING INTERNAL STRUCTURES OF THE EYEBALL AGAINST UV-A RAYS OR FOR THE TREATMENT OF KERATOCONUS WITH A TRANS-EPITHELIAL CROSS-LINKING TECHNIQUE

(75) Inventors: Salvatore Troisi, Mercato San Severino (IT); Antonio Del Prete, Naples NA (IT); Ciro Caruso, Naples NA (IT)

(73) Assignees: Renato Sanseverino, Naples NA (IT); Salvatore Troisi, Mercato San Severino SA (IT); Antonio Del Prete, Naples NA (IT); Ciro Caruso, Naples NA (IT)

( * ) Notice: Subject to any disclaimer, the term of this patent is extended or adjusted under 35 U.S.C. 154(b) by 9 days.

(21) Appl. No.: 13/387,668

(22) PCT Filed: Jul. 23, 2010

(86) PCT No.: PCT/EP2010/060752
§ 371 (c)(1),
(2), (4) Date: Jan. 27, 2012

(87) PCT Pub. No.: WO2011/012557
PCT Pub. Date: Feb. 3, 2011

(65) Prior Publication Data
US 2012/0121567 A1 May 17, 2012

(30) Foreign Application Priority Data

Jul. 27, 2009 (IT) .............................. VA2009A0052
May 20, 2010 (IT) .............................. VA2010A0044

(51) Int. Cl.
*A61K 31/122* (2006.01)
*A61K 31/5415* (2006.01)
*A61K 31/525* (2006.01)
*A61K 31/616* (2006.01)
*A61K 31/203* (2006.01)
*A61K 31/4415* (2006.01)
*A61K 31/51* (2006.01)

(52) U.S. Cl.
CPC ............ *A61K 31/203* (2013.01); *A61K 31/4415* (2013.01); *A61K 31/51* (2013.01); *A61K 31/525* (2013.01)

(58) Field of Classification Search
CPC A61K 31/122; A61K 31/525; A61K 31/5415
See application file for complete search history.

(56) References Cited

FOREIGN PATENT DOCUMENTS

| CN | 1106669 A | 8/1995 |
|---|---|---|
| CN | 1106669 A | 8/1995 |
| JP | 2005-247777 A | 9/2005 |
| WO | WO-9801136 A1 | 1/1998 |
| WO | WO-0137851 A2 | 5/2001 |
| WO | WO-0217879 A1 | 3/2002 |
| WO | WO-2009001396 A1 | 12/2008 |

OTHER PUBLICATIONS

Ayala et al., Investigative Ophthamology & Visual science, 2000.*
Wollensak, G. et al.; "Riboflavin/ultraviolet-A-induced collagen crosslinking for the treatment of keratoconus"; American Journal of Ophthalmology, Ophthalmic Publ, Chicago, IL, US, vol. 135, No. 5, May 1, 2003, pp. 620-627.
Gaby, A. R.: "Nutritional therapies for ocular disorders: Part three"; Alternative Medicine Review 200809 US, vol. 13, No. 3, Sep. 2008, pp. 191-204.
Ahlrot-Westerlund B. et al.: "Remarkable success of antioxidant treatment (selenomethionine and vitamin E) to a 34-year old patent with posterior subcapsular cataract, keratoconus, severe atopic eczema and asthma"; ACTA Opthalmologica, Apr. 1988, vol. 66, No. 2, Apr. 1988, pp. 237-238.
Rama, P. et al.: "Acanthamoeba keratitis with perforation after corneal crosslingking and bandage contact lens use"; Journal Cataract and Refractive Surgery, Surgery, Fairfax, VA; vol. 35, No. 4, Apr. 1, 2009, pp. 788-791.
Mazzotta, C. et al.: "Corneal Healing AFter Riboflavin Ultraviolet-A Collagen Cross-Linking Determined by Confocal Laser Scanning Microscopy in Vivl: Early and late Modifications"; American Journal of Ophthalmology, Ophthalmic Publ., Chicago, IL, vol. 146, No. 4, Oct. 1, 2008, pp. 527-533.
Journal of Clinical Ophthalmology, 2000, vol. 8, No. 5, pp. 366-367.
Bo et al., "The Apoptosis of Human Lens Epithelial Cell in Vitro Induces by Ultraviolet Radiation", Acta Academiae Medicinae Jiangxi, 2001; 41(5): 39-42.
Third Office Action of the Chinese Patent Application 201080032800.1 dated Jan. 8, 2014.

* cited by examiner

*Primary Examiner* — Zohreh Fay
(74) *Attorney, Agent, or Firm* — Lucas & Mercanti, LLP

(57) ABSTRACT

An ophthalmic solution containing riboflavin and at least a compound chosen in the group composed of essential and conditionally essential amino acids, coenzyme Q, L-proline, glycine, lysine hydrochloride, L-leucine, L-arginine and compounds intended to stimulate the production of metalloproteinase MMP9 for the protection of internal structures of the eyeball against UV-A rays or for the treatment of keratoconus with a trans-epithelial cross-linking technique.

13 Claims, 7 Drawing Sheets

OPHTHALMIC SOLUTION FOR PROTECTING INTERNAL STRUCTURES OF THE EYEBALL AGAINST UV-A RAYS OR FOR THE TREATMENT OF KERATOCONUS WITH A TRANS-EPITHELIAL CROSS-LINKING TECHNIQUE

CROSS REFERENCE TO RELATED APPLICATIONS

This application is a 35 U.S.C. 371 National Stage Application of International Application No. PCT/EP2010/060752, filed Jul. 23, 2010, claiming priority from Italian Application No. VA2009A000052, filed Jul. 27, 2009 and Italian Application No. VA2010A000044, filed May 20, 2010, the entire contents of which are incorporated herein by reference in their entireties.

TECHNICAL FIELD

This invention relates in general to compositions and techniques for the treatment of keratoconus and more particularly to a novel solution suitable to be used for protecting internal structures of the eyeball against UV-A or in a corneal cross-linking treatment.

BACKGROUND

The book [18] provides a review of problems and of techniques for administering and assimilating ophthalmic solutions.

Corneal cross-linking (C3) with riboflavin (vitamin B2), shortly called riboflavin-C3, is an innovative technique for treating patients affected by keratoconus and corneal ectasia and consists in administering riboflavin and ultra-violet irradiation (UV-A) for strengthening the corneal tissue [1] [2].

The cross-linking treatment is relatively simple: riboflavin in instilled in the eye and the cornea is irradiated with a properly dosed amount of UV-A rays for five minutes; the procedure is then repeated six times in succession for a total exposition to UV-A rays of 30 minutes.

The most important clinical parameter that should be taken into consideration for establishing the suitability to the cross-linking treatment is the corneal thickness, that must be not smaller than 400 microns.

The objective of this conservative treatment of keratoconus is to delay or hopefully to eliminate the need of corneal transplantation and to improve visual performances of patients by enhancing they quality of life [6] [7].

The cross-linking technique has been used for the treatment of keratoconus, a pathology characterized by a progressive weakening of the cornea for an anomalous laxity of corneal parenchyma due to a reduced cohesion of collagen lamellae of which it is composed. By using UV-A rays and riboflavin, new links among adjacent corneal collagen molecules are created and the treated corneas are thicker and stiffer [3]. Corneas have numerous layers of collagen fibers in the thickness of the parenchyma; the transversal links, the so-called "cross-links" that tie the various layers of collagen among them, contribute in a determinant fashion to the corneal stiffness. The objective of the corneal cross-linking treatment is to increase the degree of rigidity of the corneal tissue through the generation of a greater number of these transversal links.

Topical application of riboflavin on the disepithelized cornea with penetration of about 200 μm and irradiation of riboflavin molecules by UV-A determine the loss of chemical equilibrium of riboflavin molecules with the consequent generation of free radicals. Riboflavin molecules become unstable and stabilize themselves by linking with two collagen fibrils. A series of biochemical "bridges" are formed among collagen fibrils (i.e. cross-linkings) such to produce a general strengthening of the cornea [3].

Actually, the treatment is carried out after having removed the outermost layer of the corneal (i.e. the corneal epithelium). This way of executing the cross-linking treatment (C3-R) of keratoconus and of corneal ectasiae contemplates the preliminary removal of corneal epithelium for favoring penetration of the standard solution of riboflavin-dextran 0.1% (for example the solution marketed by SOOFT ITALIA S.r.l. under the trademark RICROLIN™) in the underlying stroma and the treatment has been standardized under these conditions. According to supporters of this technique, the removal of the epithelial layer would be necessary for ensuring the best possible absorption of the riboflavin solution inside the corneal stroma and thus the maximum effectiveness of the therapy.

Unfortunately, the removal of the corneal epithelium may cause ocular itches or burn the day after the treatment and in the immediately successive days and transient blurring; these symptoms are well known and persist until the corneal epithelium has not been restored and are usually treated, in the successive days [4-7] after the C3-R, with non-steroidal anti-inflammatory (NSAID) eye drops, with eye drops based on tear substitutes and analgesics, and with the application of a therapeutic contact lens on the cornea.

Several authors sustain that it could be possible to execute the C3-R treatment by applying the standard methodology without preliminary removal of corneal epithelium, and that such a treatment would be effective and safe as demonstrated by the observed clinical data. According to this technique, the treatment should be executed without preliminarily removing the corneal epithelium (disepithelization). The objective is to avoid that patients experience diseases due to the epithelium removal, intrinsic of the first method, to execute the treatment in an ambulatory and in particular to avoid any risk of post-surgical infections intrinsic in the treatment that contemplates the epithelium removal with a consequent exposition of underlying layers of the cornea. Supporters of this way of executing the treatment suggested to apply riboflavin on the eye for a longer time interval for allowing a better absorption of riboflavin in the stroma before irradiating with UV-A rays [8].

As far as the removal or not of the epithelium is concerned in the treatment with cross-linking of keratoconus and of corneal ectasiae in general, contrasting opinions are reported in literature. The C3-R treatment has been studied and implemented after having removed the corneal epithelium for favoring the penetration of riboflavin in the stroma. To the best knowledge of the authors, no study is available in literature for determining whether or not and how much riboflavin penetrates in corneal stroma [9] by removing or without removing the corneal epithelium.

The execution of cross-linking without preliminary disepithelization has been criticized by numerous authors, who sustain that in this way riboflavin would not pass through the epithelium and that it has not yet been demonstrated whether or not and how much standard solution of riboflavin-dextran 0.1% effectively penetrates in the corneal stroma without removing the epithelium and whether or not the treatment by UV-A rays in a trans-epithelial fashion result equally effective as that carried out after removal of corneal epithelium.

In an attempt to provide effective substances for treating keratoconus with cross-linking technique without removing the corneal epithelium, Dr. Spörl suggested [17] to use benzalkonium chloride for increasing permeability of epithelium and Dr. Pinelli suggested to use tensioactives mixed with riboflavin.

The Italian patent application No. MI2007A002162 [16] discloses a novel solution for the treatment of keratoconus with a trans-epithelial cross-linking technique containing riboflavin and benzalkonium chloride.

Experiments executed by the applicants on human corneas, the results of which are illustrated hereinafter, lead to the conclusion that the second technique carried out using the standard solution or the composition proposed by Dr. Pinelli [16] would not overcome the problems due to the removal of corneal epithelium because it would be destroyed, leaving exposed the underlying layers with consequent risks of infections and alterations of repairing mechanisms. It would be desirable to have a composition containing riboflavin for executing the corneal cross-linking that be capable to cross the corneal epithelium in relatively short times and that do not damage the corneal epithelium, that is the cause of annoying post-surgical symptoms.

SUMMARY

The applicants carried out intensive studies aimed to determine how much riboflavin penetrates alone or mixed with other products ("permeation enhancers") through human corneas with and without preliminary removal of corneal epithelium, as well as the effectiveness and safety of the successive treatment with UV-A rays.

Several useful substances have been identified, chosen in the group composed of essential and conditionally essential (such as arginine, cysteine, glycine, glutamine, histidine, proline, serine and tyrosine) amino acids, coenzyme Q, vitamin E, L-proline, glycine, lysine hydrochloride, L-leucine, L-arginine and compounds intended to stimulate the production of metalloproteinase MMP9, more precisely identified hereinafter, that may be effectively used as carriers ("permeation enhancers") in ophthalmic solutions suitable to the administration of riboflavin, in particular with the standard solution of riboflavin-dextran, through the corneal epithelium. The so-obtained ophthalmic solutions, that may be marketed for example in the form of eye drops or of gel or of water solutions or emulsion or applied on therapeutic contact lenses, may be used for the treatment of keratoconus with a trans-epithelial cross-linking technique thus preserving the corneal epithelium.

Ophthalmic solutions may eventually contain excipients, such as for example acetic acid, or the above mentioned substances may be treated with acetic acid or with another excipient before being mixed with riboflavin.

This invention further propose the use of at least a substance chosen in the group composed of essential and conditionally essential amino acids, coenzyme Q, vitamin E, L-proline, glycine, lysine hydrochloride, L-leucine, L-arginine and compounds intended to stimulate the production of metalloproteinase MMP9, more precisely identified hereinafter, for the preparation of an ophthalmic solution containing riboflavin intended to protect internal structures of the eyeball against UV-A rays or to treat keratoconus with a trans-epithelial cross-linking technique and a relative ophthalmic solution containing riboflavin, and as carrier ("permeation enhancer") in a composition suitable for administering riboflavin through corneal epithelium.

This invention proposes also a method of preparing such an ophthalmic solution consisting in adding to a riboflavin solution at least one of the above-identified carriers.

Each of the proposed substances as a carrier may be added alone or in combination with other proposed carriers to a solution containing riboflavin at concentrations chosen in the ranges indicated in the ensuing description of exemplary embodiments.

The invention is defined in the annexed claims.

DESCRIPTION OF EXEMPLARY EMBODIMENTS

Figure 1:
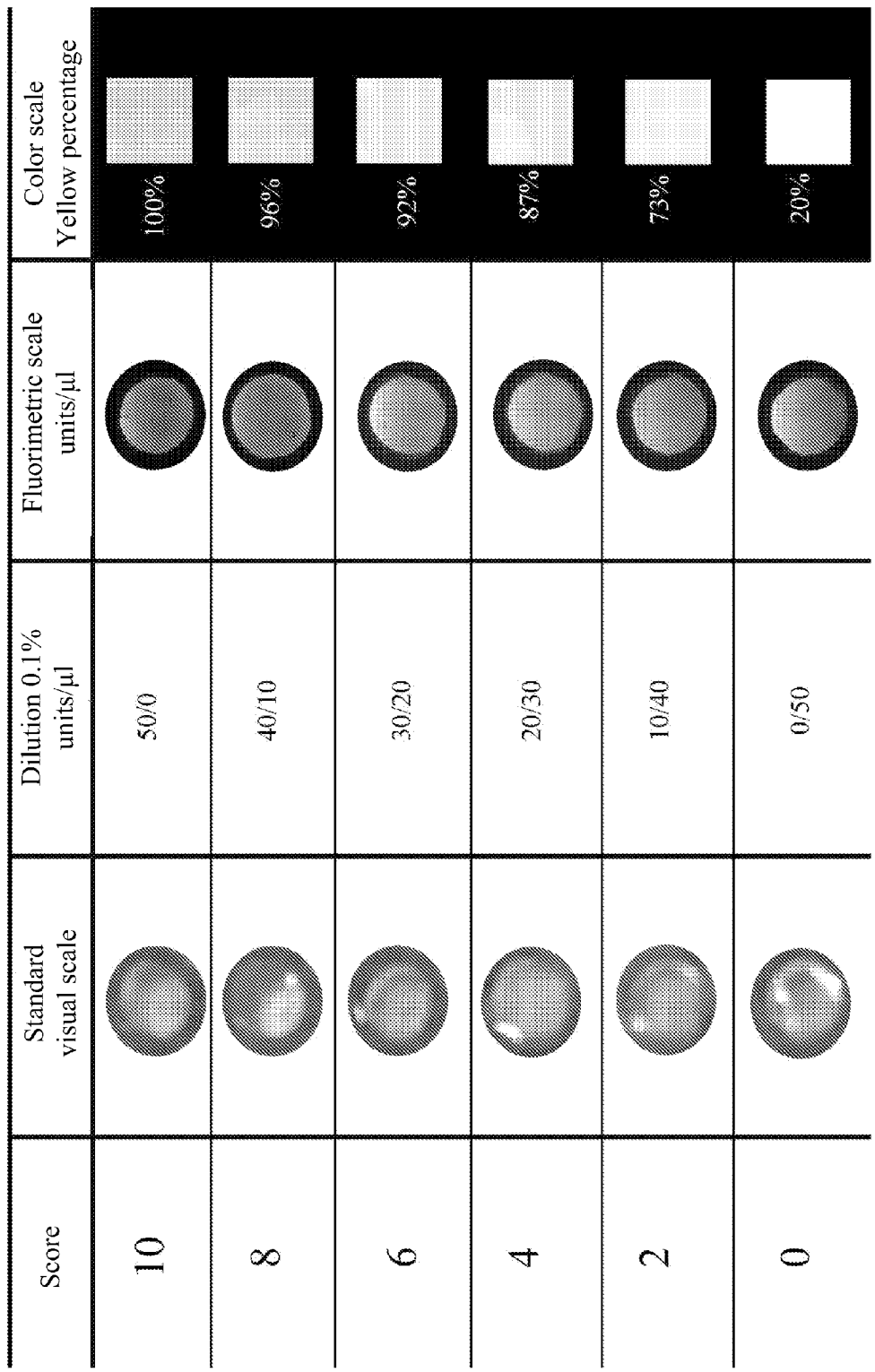
FIG. 1 shows a visual, fluorimetric, colorimetric evaluation scale adopted for assessing the passage of riboflavin solution 0.1% through the cornea after application in a trans-epithelial fashion.

All tests have been executed on human corneas of donors, coming from Azienda Ospedaliera Napoli 1—Banca Occhi ("Eye Bank")—Regione Campania—Ospedale dei Pellegrini after consensus as contemplated in the explantation protocol and pursuant to the permission of the Ethical Committee—docket No. 0009304/2009—Decision No. 1269.

The penetration of the tested compositions through integer human corneas, i.e. without preliminary removal of epithelium, has been observed, the corneas having a thickness comprised between 500 and 600 microns, the compositions being the standard solution of riboflavin-dextran, the composition made of riboflavin-dextran plus benzalkonium chloride suggested in [16] and [17], and the novel test compositions obtained by mixing riboflavin with at least a substance chosen in the group comprising vitamin E, coenzyme Q, L-proline, glycine, lysine hydrochloride, L-leucine, with certain concentrations.

The concentrations of the used substances for realizing the novel test compositions are comprised in the following ranges:

vitamin E: concentration from 0.0001 mg % ml to 2000 mg % ml. According to a more preferred embodiment, the concentration ranges from 0.01 mg % to 1500 mg % ml. According to a yet more preferred embodiment, the concentration ranges from 10 mg % ml to 1000 mg % ml. According to a yet more preferred embodiment, the concentration is about 500 mg % ml;

vitamin Q: concentration from 0.0001 mg % ml to 2000 mg % ml. According to a more preferred embodiment, the concentration ranges from 0.01 mg % to 1500 mg % ml. According to a yet more preferred embodiment, the concentration ranges from 1 mg % ml to 1000 mg % ml. According to a yet more preferred embodiment, the concentration is about 100 mg % ml;

L-proline: concentration from 0.0001 mg % ml to 2000 mg % ml. According to a more preferred embodiment, the concentration ranges from 0.001 mg % to 100 mg % ml. According to a yet more preferred embodiment, the concentration ranges from 0.005 mg % ml to 10 mg % ml. According to a yet more preferred embodiment, the concentration ranges from 0.01 mg % ml to 1 mg % ml. According to a yet more preferred embodiment, the concentration is about 0.1 mg % ml;

glycine: concentration from 0.0001 mg % ml to 2000 mg % ml. According to a more preferred embodiment, the concentration ranges from 0.001 mg % to 100 mg % ml. According to a yet more preferred embodiment, the concentration ranges from 0.005 mg % ml to 10 mg % ml. According to a yet more preferred embodiment, the concentration ranges from 0.01 mg % ml to 1 mg % ml. According to a yet more preferred embodiment, the concentration is about 0.1 mg % ml;

lysine hydrochloride: concentration from 0.0001 mg % ml to 2000 mg % ml. According to a more preferred embodiment, the concentration ranges from 0.001 mg % to 100 mg % ml. According to a yet more preferred embodiment, the concentration ranges from 0.005 mg % ml to 10 mg % ml. According to a yet more preferred embodiment, the concentration ranges from 0.01 mg % ml to 1 mg % ml. According to a yet more preferred embodiment, the concentration is about 0.05 mg % ml;

L-leucine: concentration from 0.0001 mg % ml to 2000 mg % ml. According to a more preferred embodiment, the concentration ranges from 0.001 mg % to 100 mg % ml. According to a yet more preferred embodiment, the concentration ranges from 0.005 mg % ml to 10 mg % ml. According to a yet more preferred embodiment, the concentration ranges from 0.01 mg % ml to 1 mg % ml. According to a yet more preferred embodiment, the concentration is about 0.08 mg % ml.

Novel solutions suitable for the treatment of keratoconus by trans-epithelial cross-linking or for protecting eyeballs against UV-A rays, have been obtained by mixing one or a plurality of the above-mentioned substances in concentrations comprised in the indicated ranges with a solution containing riboflavin, for example with a riboflavin-dextran solution in a concentration chosen in the range from 0.0001% to 0.5%. According to a more preferred embodiment, the riboflavin-dextran concentration ranges from 0.001% to 0.4%. According to a yet more preferred embodiment, the concentration ranges from 0.005% to 0.3%. According to a yet more preferred embodiment, the concentration ranges from about 0.01% to 0.2%. According to a yet more preferred embodiment, the concentration is about 0.1%.

The results of the tests have shown that each of the substances of the identified group is suitable for favoring penetration of riboflavin and in particular of the standard riboflavin-dextran solution, through the corneal epithelium and to protect the cornea against UV-A rays.

The corneas taken into consideration for the test, discarded from the eye bank because unusable for transplantation, have been kept into appropriate solutions and before the tests they were evaluated again by means of optical microscopy and examination of endothelial cells.

Only corneas with good transparency have been used, with a thickness ranging between 500 and 600 microns with good endothelial mosaic, according to what is suggested in [10-15].

Corneas have been positioned such to shut a cylindrical chamber containing a predetermined solution of sodium hyaluronate plus xanthan gum 0.4 ml. A waterproof sealing metal ring having the same diameter of the cylindrical box was applied on the corneal surface. Then the compositions to be tested containing a fluorescent substance (riboflavin) were applied on the corneas. By measuring the fluorescence of the solution inside the box at various instants, it has been possible to determine in which amount the novel solutions penetrate in the cornea and how long the solutions take for this.

The effectiveness of the indicated substances as carrier in compositions for administering riboflavin in a trans-epithelial fashion and of compositions obtained by mixing riboflavin with at least one of the indicated substances is described through the following test examples, only for illustrative and non limitative purposes.

For the sake of brevity, only the results of tests obtained by treating corneas with the following compositions are reported:
1) Standard solution of riboflavin-dextran 0.1%;
2) Standard solution of riboflavin-dextran 0.1%+benzalkonium chloride 0.01% according to [16];
3) First novel test composition of riboflavin-dextran 0.1%+vitamin E TPGS (D-alpha-tocopheryl tocopheryl polyethylene glycol 1000 succinate) at the concentration of 500 mg % ml;
4) Second novel test composition of riboflavin-dextran 0.1%+vitamin Q 100 mg % ml;
5) Third novel test composition of riboflavin-dextran 0.1%+L-proline 0.1 mg %+glycine 0.1 mg %, lysine hydrochloride 0.05 mg %+L-leucine 0.08 mg %;
6) Fourth novel test composition of riboflavin-dextran 0.1%+vitamin E (D-alpha-tocopheryl polyethylene glycol 1000 succinate) 500 mg % ml+vitamin Q 100 mg % ml+L-proline 0.1 mg %+glycine 0.1 mg %+lysine hydrochloride 0.05 mg %+L-leucine 0.08 mg %.

Each of the six mentioned compositions has been applied on the surface of corneas selected and placed as described above and soaking of corneal stroma has been evaluated after 15 minutes and after 30 minutes together with the presence of fluorescent substance in the solution of sodium hyaluronate+xanthan gum 0.4 ml placed inside the container below the treated cornea. The evaluation of riboflavin penetration in the corneal stroma has been carried out by sectioning the cornea and by successive evaluation with a fluorescence microscope.

The presence of riboflavin inside the solution of sodium hyaluronate+xanthan gum 0.4 ml, that demonstrates the passage through the cornea, has been evaluated both qualitatively by using a visual and fluoroscopic scale as depicted in FIG. 1, as well as quantitatively by using a colorimetric scale. The two numbers near each color sample represent respectively the number of parts of standard solution of riboflavin that causes the shown color and the number of parts of solution of xanthan gum and sodium hyaluronate. The reference scale has been defined by preparing dilutions of riboflavin-dextran 0.1% with xanthan gum+sodium hyaluronate in the following proportions (units/ml): 50/0, 40/10, 30/20, 20/30, 10/40, 0/50. A visual scale and a fluorimetric scale corresponding to the defined values of units/ml has been prepared and a score from 10 down to 0 for each dilution ratio has been allotted. The colorimetric scale contemplates a minimum value of percentage of yellow equal to 20% in absence of riboflavin, corresponding to the colorimetric spectrum of the substance chosen as diluent.

The evaluation by a visual scale has been carried out in standard illumination conditions by direct comparison of samples obtained by tests with the predefined sample and by digital photographic techniques. The fluorimetric evaluation has been carried out using a fluorescence scanning microscope equipped with a digital photocamera in a dark room. The score relative to the evaluation with a visual and fluorimetric scale has been carried out by a third examiner, by carrying out an average of the values obtained with the two methods.

The colorimetric evaluation has been carried out by inserting the material present at the end of the experiment inside the cylindrical chamber (and thus below the cornea) in a transparent bag and with a computer analysis, by scanning at high definition the pre-defined dilutions and evaluating of the yellow percentage using the software program Photoshop™ 7.0 and a monochrome filter. With this technique it has been possible to compare the detected yellow percentage, in the samples of the experiment with precisely determined concentration values expressed in units/ml of the standard riboflavin 0.1% solution as shown in FIG. 1.

Figure 2A:
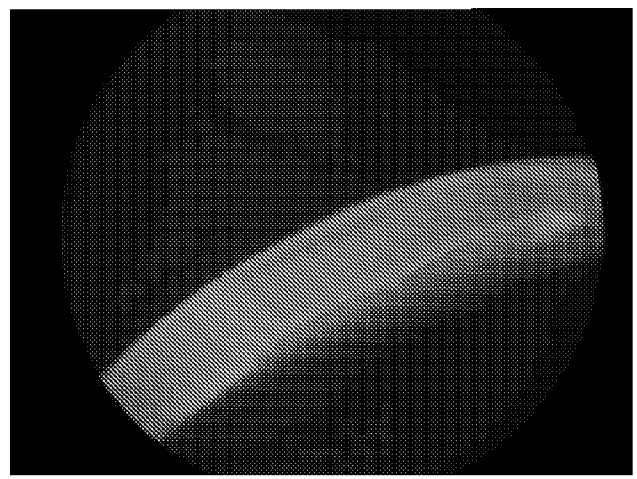
FIG. 2a is a fluoroscopic picture of a section of a cornea on which the fourth test composition has been applied in a trans-epithelial fashion, after 15 minutes.
Figure 2B:
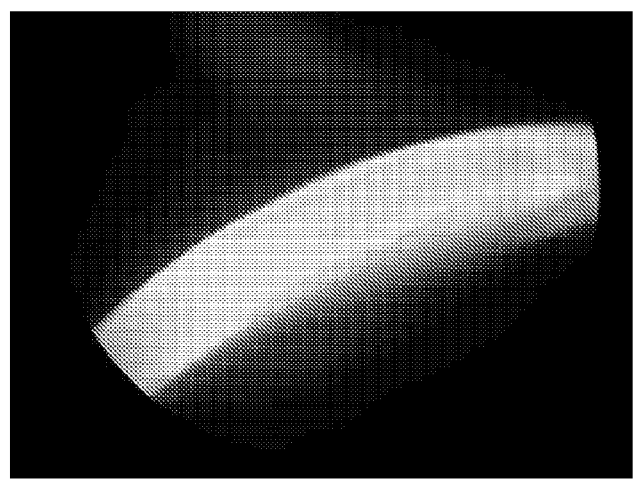
FIG. 2b is a fluoroscopic picture of a section of a cornea on which the fourth test composition has been applied in a trans-epithelial fashion, after 30 minutes.
Figure 2C:
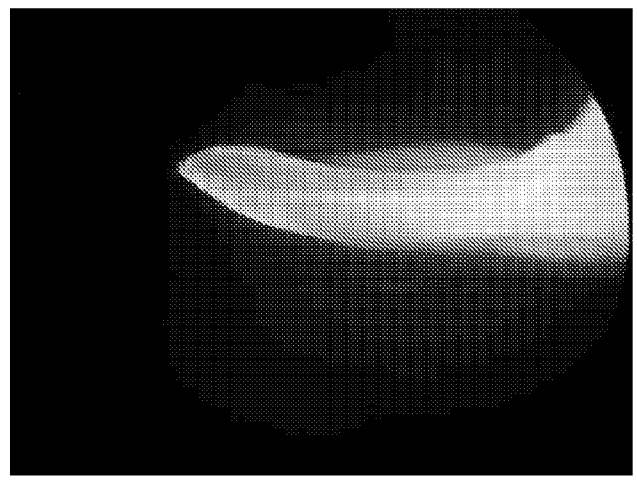
FIG. 2c is a fluoroscopic image of a section of a cornea treated with trans-epithelial cross-linking using the fourth novel solution, in which the intense fluorescence because of the passage of the fourth composition and the relevant rigidity of the tissue after the treatment may be noticed.

FIG. 2a is a fluoroscopic image of a section of a cornea treated with trans-epithelial cross-linking after having applied the fourth novel solution for 15 minutes, FIG. 2b is a fluoroscopic image of a section of a cornea treated with trans-epithelial cross-linking after having applied the fourth novel solution for 30 minutes, and FIG. 2c is a fluoroscopic image of a section of a cornea treated with trans-epithelial cross-linking with the fourth novel solution. In this last figure it is possible to notice that riboflavin has penetrated in the whole cornea and that the tissue is stiffer after the cross-linking treatment.

The performed tests showed that:
a) after 15 minutes from the application of the standard solution of riboflavin-dextran 0.1% in a trans-epithelial fashion, the corneal stroma is partially soaked and the fluorescent solution is not detectable in the substance inside the container, the colorimetric spectrum being superposable to the solution of sodium hyaluronate+xanthan gum 0.4 ml (score 0 as in FIG. 1 and yellow percentage not greater than 20%);
b) after 30 minutes from the application of the standard solution of riboflavin-dextran 0.1% in a trans-epithelial fashion, the corneal stroma appears completely soaked of fluorescent solution; the fluorescence in the solution of sodium hyaluronate+xanthan gum 0.4 ml in the container may be detected, with a score 2-3 of FIG. 1 and yellow percentage determined with the above-mentioned computer-implemented technique in a range 75%-80%;
c) after 15 minutes from the application in a trans-epithelial fashion of the first novel test solution of riboflavin-dextran 0.1%+vitamin E TPGS (D-alpha-tocopheryl polyethilenglycol 1000 succinate) at the concentration of 500 mg % ml, the cornea is completely soaked and the fluorescent solution is present inside the container (score 2-3 of FIG. 1, with a yellow percentage of 72-76%);
d) after 30 minutes from the application of the first novel test solution, all layers of the cornea are completely soaked and there is a high concentration of riboflavin inside the container, showing a good permeability of the corneal tissue to the product itself in contact with the epithelial surface (score 3-4 of FIG. 1, with yellow percentage of 79-84%);
e) the composition proposed in [16] and the novel test solutions second and third, containing, respectively: benzalkonium chloride 0.01%; vitamin Q 100 mg % ml; L-proline 0.1 mg %, glycine 0.1 mg %, lysine hydrochloride 0.05 mg % and L-leucine 0.08 mg %, showed, under the same conditions, a better penetration of riboflavin both in quantitative terms as well as in terms of rapidity of penetration, than the corresponding results obtained using the standard solution alone (riboflavin-dextran 0.1%) (score 3-4 of FIG. 1 after 15 minutes and a score 4-6 after 30 minutes, with a yellow percentage of 70-79% after 15 minutes and of 78-86% after 30 minutes);
f) the fourth novel test composition gave even better results than all the other tested compositions. The different concentrations of colorant detected in a fluoroscopic manner and the computer-implemented analysis of the fluorescent substance inside the container after 15 minutes and after 30 minutes of application of the product on the epithelium surface are outstandingly enhanced (score 5-6 of FIG. 1 after 15 minutes, with a yellow percentage of 88-91%; score 6-7 after 30 minutes, with a yellow percentage greater than 90%); the greater concentration of fluorescent substance in the solution placed below the cornea, obtained after trans-epithelial application of the fourth novel test solution, is particularly evident after 15 minutes, especially if compared with the results obtained using the standard solution, that is not even detectable in the solution placed inside the container after a same time interval. This may be explained supposing that there is a synergistic effect among the permeation enhancers when mixed together, for favoring the passage of riboflavin through the corneal epithelium.

The illustrated results show that at least the following substances:

vitamin E

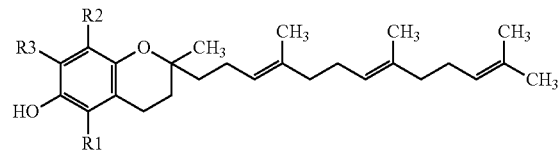

R1=CH$_3$ or H R2=CH$_3$ or H R3=CH$_3$; merely for example, vitamin E TPGS (D-alpha-tocopheryl polyethilenglycol 1000 succinate) may be cited;

coenzyme Q

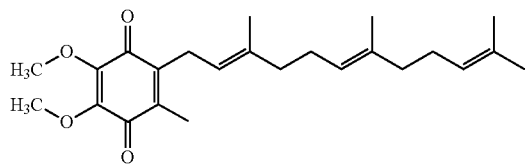 [SMILES: COC1=C(OC)C(=O)C(C/C=C(\C)CC/C=C(\C)CCC=C(C)C)=C(C)C1=O]

in the oxidized form,

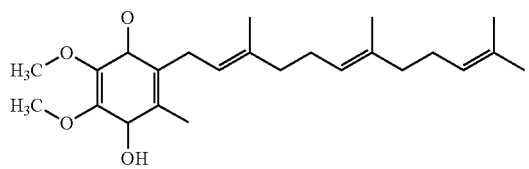 [SMILES: COC1=C(OC)C(O)C(C/C=C(\C)CC/C=C(\C)CCC=C(C)C)=C(C)C1O]

in the half-quinonic form,

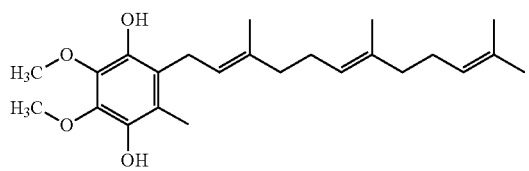 [SMILES: COc1c(O)c(C)c(C/C=C(\C)CC/C=C(\C)CCC=C(C)C)c(O)c1OC]

in the reduced form,
whichever the number of isoprenoid units of coenzyme Q is; only for example, the coenzyme Q10 may be cited;

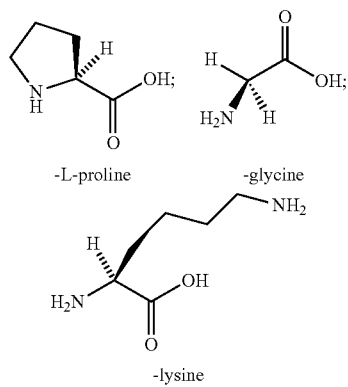

-L-proline                -glycine

-lysine or lysine hydrochloride;

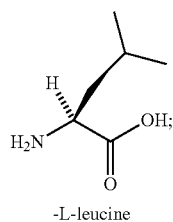

-L-leucine alone or in combination among them, eventually in combination with excipients such as acetic acid and in concentration chosen in the ranges mentioned above, facilitate the penetration of riboflavin through the corneal epithelium in shorter time intervals than the time intervals required by the standard riboflavin-dextran solution and in amounts sufficient for the successive cross-linking treatment.

The combination of all mentioned compounds with riboflavin showed an unsuspected synergistic effect in producing better results from the point of view of the concentration of product that crosses the corneal tissues and the rapidity with which it penetrates.

The applicants tested in vitro the effectiveness of the trans-epithelial cross-linking treatment on human corneas by applying the fourth novel test composition and UV-A irradiation of 3 $mW/cm^2$, according to the standard protocols. The tested corneas have been prepared as in the previous experiment, by fixing them onto an appropriate bearing and by applying the standard solution of riboflavin-dextran 0.1% and the fourth novel test composition on the epithelium surface (thus administered in a trans-epithelial fashion) of respective corneas for thirty minutes. Successively, the standard UV-A irradiation has been executed for thirty minutes, subdivided into steps of 5 minutes, preceded by re-administration of each solution on the surface of the cornea. At the end of the experiment, the degree of rigidity of the cornea has been evaluated as follows: each cornea has been maintained by an end portion for a length of 2 mm with corneal forceps kept aligned to a horizontal line and the angle formed by the opposite end of the cornea in respect to the horizontal line has been measured.

Figure 3A:
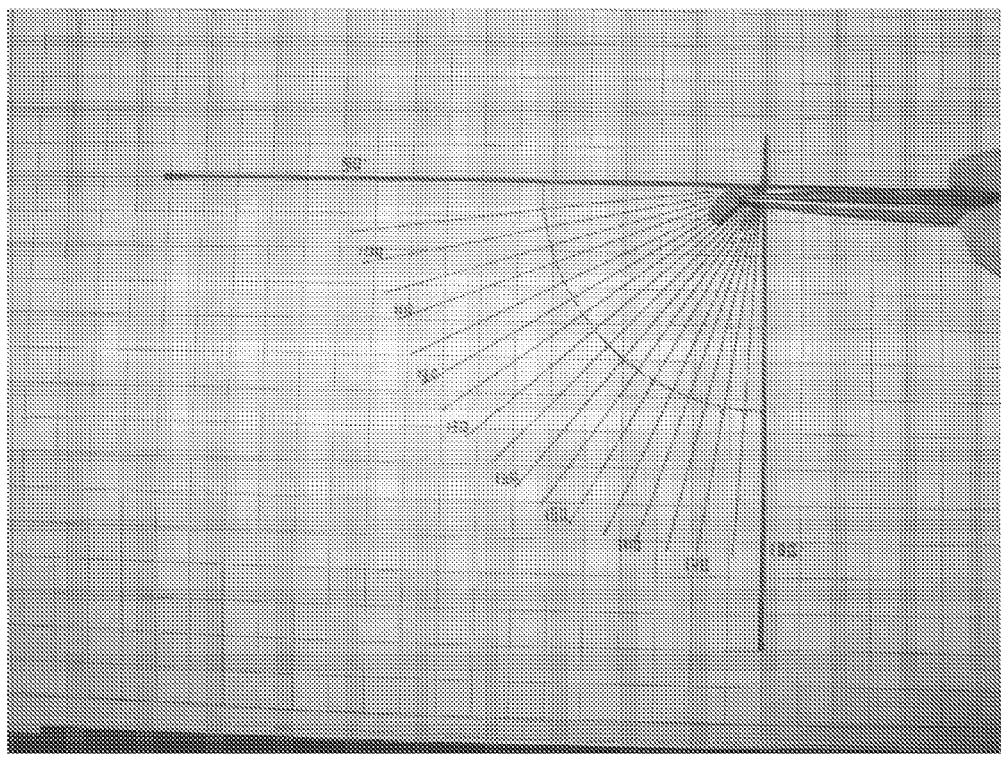
FIG. 3a shows the deflection degree of a cornea treated with trans-epithelial cross-linking using the standard solution.
Figure 3B:
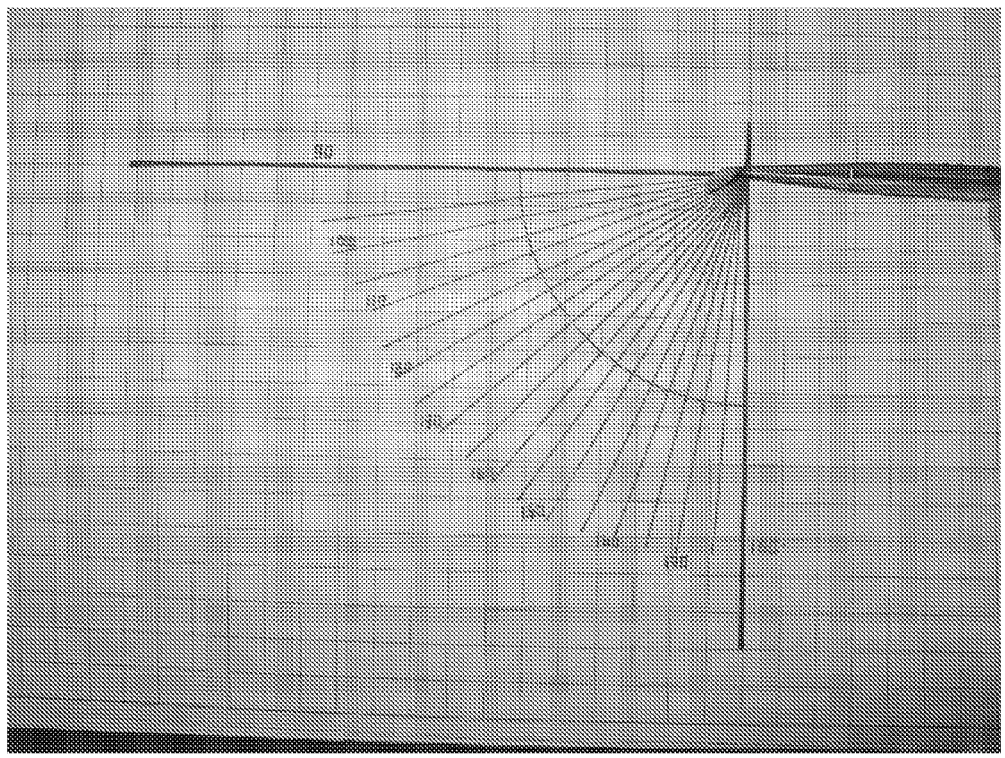
FIG. 3b shows the deflection degree of a cornea treated with trans-epithelial cross-linking using the fourth novel test solution.

FIG. 3a shows a cornea after trans-epithelial cross-linking treatment carried out using the standard solution of riboflavin-dextran 0.1%, that bends downwards by about 40° and FIG. 3b shows another cornea after the cross-linking treatment carried out using the fourth novel test composition and without having preventively removed the corneal epithelium. By comparing the two figures, it is evident that the trans-epithelial cross-linking treatment carried out with the fourth novel test composition has strengthened the cornea, as desired, that bends downwards by only 25°.

As a further confirmation of the effectiveness of the trans-epithelial cross-linking treatment by using the fourth novel test composition, this treatment has been implemented in vitro on human corneal end portions, belonging to patients affected by keratoconus, subjected to perforating keratoplastic; in these cases the cornea explanted from the patient, instead of being destroyed, has been used in a laboratory, paying attention to avoid the surgery time relative to diathermy, such to allow the preservation of the planes of the corneal layers (full thickness transplantation). The corneal limbs have been fixed onto an appropriate bearing. The standard solution of riboflavin-dextran 0.1% has been applied on the first cornea, and the fourth novel test solution has been applied on the second cornea, by applying for thirty minutes the solutions on the corneal surfaces without removing the epithelium. Successively, the standard 340 nm UV-A treatment has been performed only on the cornea treated with the fourth novel test solution at a power of 3 $mW/cm^2$ for thirty minutes subdivided into steps of 5 minutes each, preceded by re-administration of the composition on the surface of the cornea. The other end portion with keratoconus, fixed on an appropriate support, has been treated only by deposition on the corneal of the standard solution of riboflavin-dextran 0.1% without successive irradiation with UV-A. At the end of the experiment, an inspection of the corneal parenchyma has been executed with a scanning electron microscopy.

Figure 4:
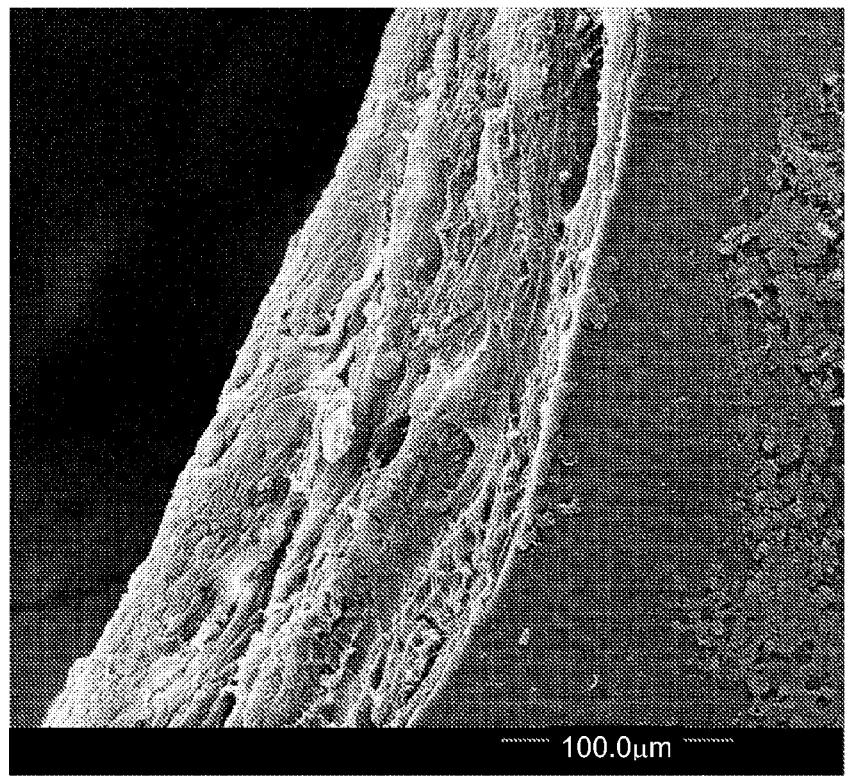
FIG. 4 is a scanning microscopy that shows lamellae in a section of a keratoconus affected cornea.
Figure 5:
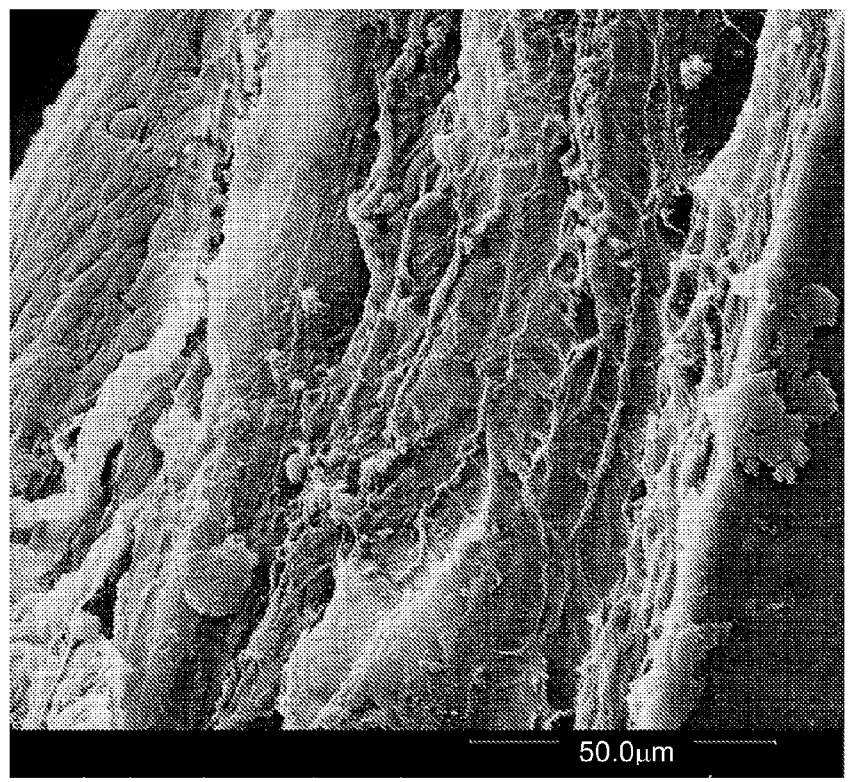
FIG. 5 is a scanning microscopy that shows an enlarged view of the cornea of FIG. 4.

FIG. 4 illustrates how lamellae of a section of a cornea coming from a patient affected by non-treated keratoconus, appear in a scanning microscopy. FIG. 5 is an enlarged view of a portion of FIG. 4. These two figures show a weakening of corneal lamellae in an end portion of the cornea on which the standard solution of riboflavin-dextran 0.1% has been applied without irradiating UV-A thereon.

Figure 6:
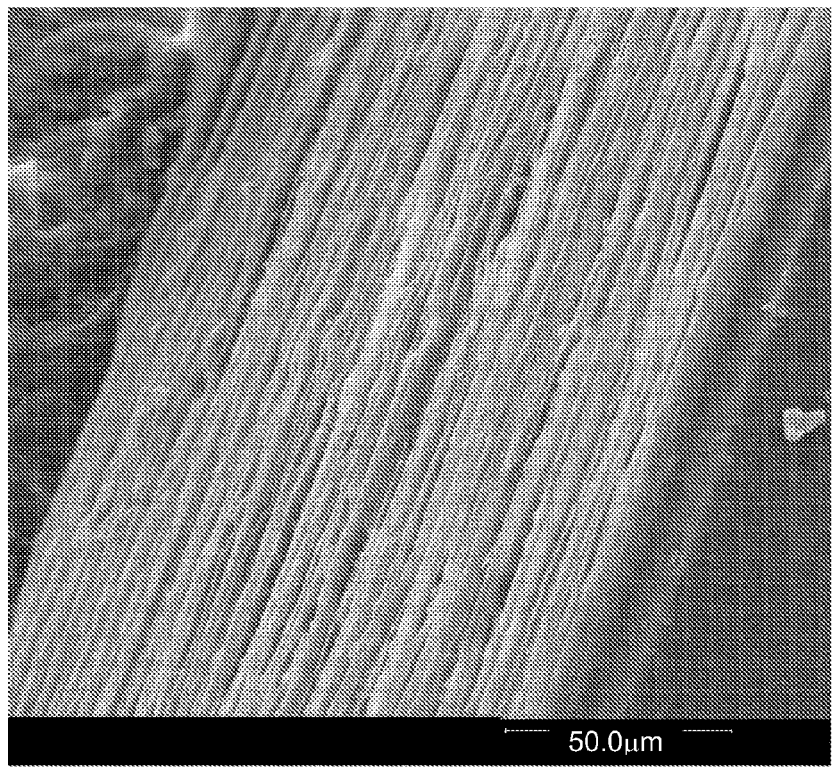
FIG. 6 is a scanning microscopy that shows lamellae in a section of a keratoconus affected cornea after the trans-epithelial cross-linking carried out using the fourth novel test composition.

FIG. 6 is a scanning microscopy that shows how lamellae of a corneal section affected by keratoconus appear after the trans-epithelial cross-linking treatment with the novel fourth test solution. The keratoconic end portion, treated with the fourth novel solution administered in a trans-epithelial fashion and irradiated with UV-A rays according to the standard protocol for thirty minutes, presented highly densely distributed and compact corneal lamellae, that demonstrate that novel biochemical cross-linkings have been formed.

Good results have been obtained also with the novel test composition first, second and third.

The obtained results using the novel test compositions overcome also the objections raised by certain authors about a hypothetical reduction of effects of the cross-linking treatment when executed in a trans-epithelial fashion, because epithelium would shield UV-A rays. The hypothesis of a reduction of the effectiveness of the trans-epithelial cross-linking treatment is wrong, as proven by the obtained histological samples, when at least one of the herein proposed substances as a carrier (permeation enhancer) is added to riboflavin and irradiation is executed according to the standard protocol.

Moreover, a comparative study of the effects of the cross-linking treatment in a trans-epithelial fashion on the morphological integrity or not of the epithelial layers of the cornea and of the microvilli present on the surface of the epithelial cells, has been carried out using a scanning electron microscope (7500×). This has been done for evaluating tolerability of the cross-linking treatment carried out with the fourth novel test composition in a trans-epithelial fashion on the corneal epithelium in respect to the standard solution of riboflavin-dextran 0.1% and to the standard composition+benzalkonium chloride 0.01%, as proposed in [16].

This test has been carried out because the epithelial cells are the first organic structures irradiated by the UV-A flux and could undergo to injuries because of absorption of these radiations. None of the available publications seems to consider this aspect, neither relative data are available in literature.

The parameters considered the most reliable for evaluating the vitality of epithelial cells are the cytological examination with an impression technique and, in particular, the examination with the electronic microscope of microvilli of the layer of superficial epithelium cells of the cornea. The presence of extroflexions of the membrane (microvilli) of the integer superficial cellular elements, containing a high concentration of mucins trans-membrane and a good glycocalyx, allow to link in an optimal fashion the free mucin that constitutes the deep layer of the pre-corneal tear film. By contrast, a pathological loss of microvilli determines a difficult adhesion of the layer of tears to the ocular surface and phenomena of epithelial suffering induced by the dysfunction of the pre-corneal tear film itself and, as a consequence, inflammations.

The morphology of microvilli has been evaluated with a scanning electron microscopy after trans-epithelial treatment in vitro with UV-A according to the standard doses. Human corneas with a thickness between 500 and 600 microns have been subjected to incubation for thirty minutes with a balanced salt solution (BSS), with the standard solution of riboflavin-dextran 0.1%, with the standard solution+benzalkonium chloride 0.01% and with the fourth novel test composition, respectively.

Preliminarily, also the morphology of microvilli and of superficial layers of the corneal epithelium of corneas not subjected to any treatment has been studied for highlighting how epithelial cells and their microvilli should appear when not subjected to any photochemical treatment.

Figure 7:
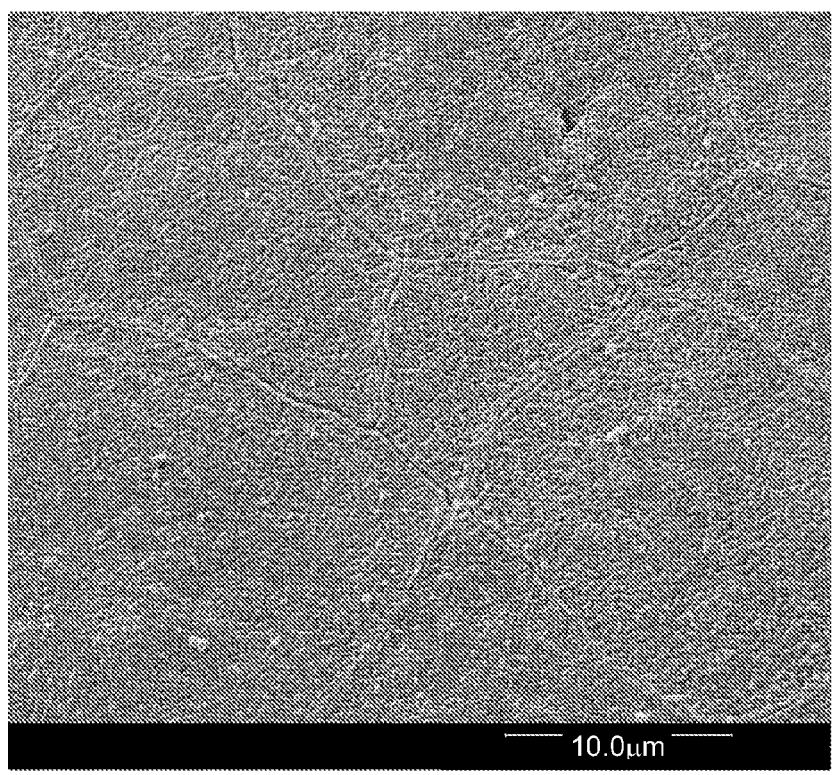
FIG. 7 is a scanning microscopy that shows morphology of microvilli and of superficial layers of the epithelium in a normal cornea.
Figure 8:
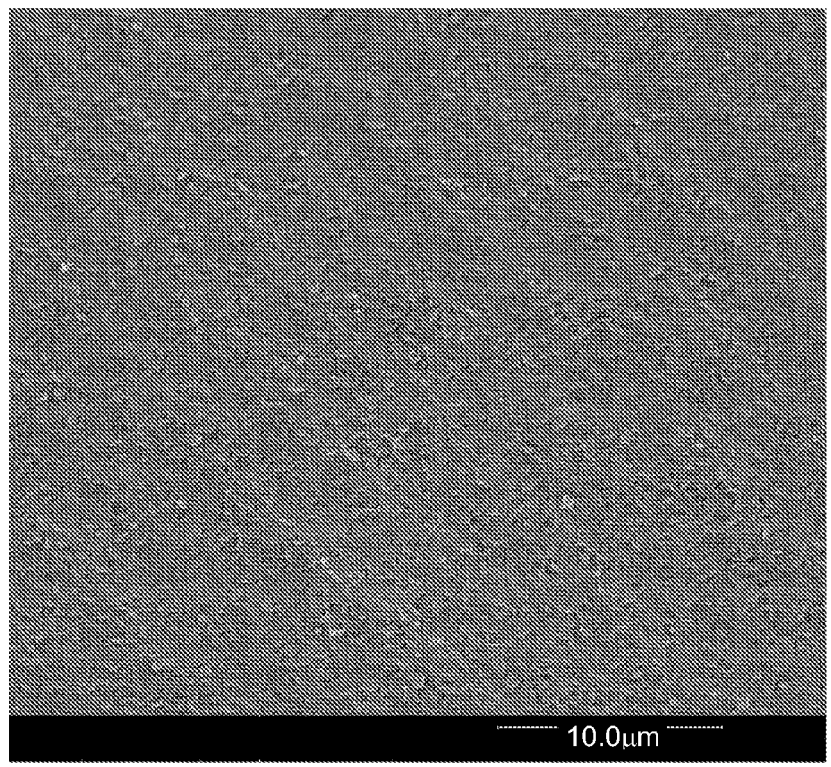
FIG. 8 is a scanning microscopy of a cornea treated with a standard dose of UV-A rays after having applied in a trans-epithelial fashion the standard solution of riboflavin-dextran 0.1%.

FIG. 7 is a scanning microscopy that show the morphology of microvilli and of superficial layers of the epithelium in a normal cornea, and FIG. 8 shows a scanning microscopy of a cornea treated with UV-A after having applied the standard solution of riboflavin-dextran 0.1% according to the standard protocol. By comparison with FIG. 7, it is evident that all epithelial layers are lost and the Bowman's membrane is uncovered.

A similar situation takes place also in those corneas treated with the composition constituted by the standard solution+benzalkonium chloride 0.01% as suggested in [16].

Figure 9:
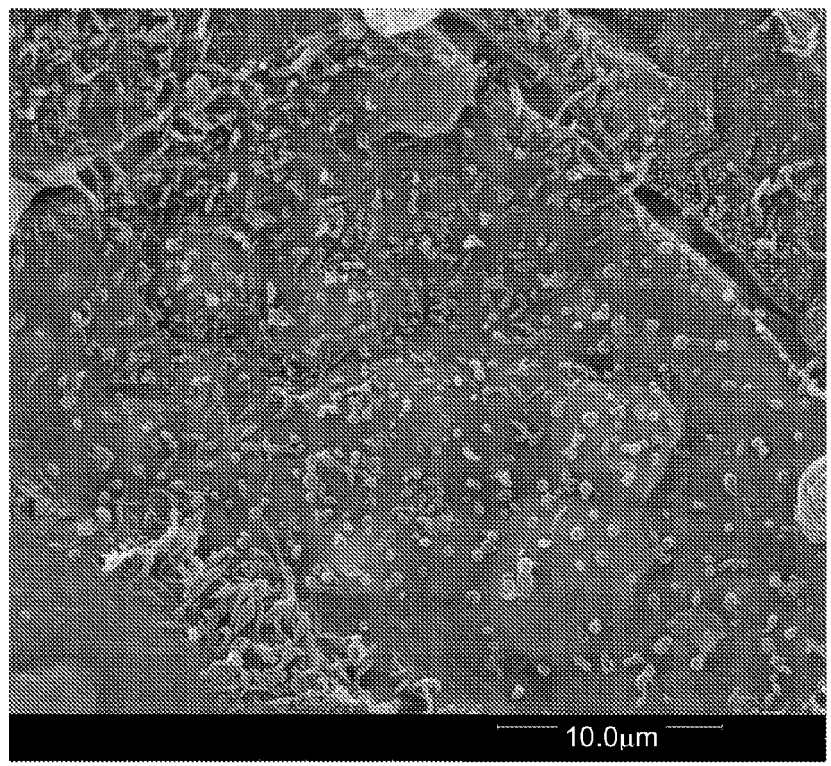
FIG. 9 is a scanning microscopy of a cornea treated with a standard dose of UV-A after having applied in a trans-epithelial fashion the fourth novel test composition.

FIG. 9 is a scanning microscopy of a cornea treated with UV-A at a standard dose after treatment with the fourth novel test composition. By comparison with FIGS. 7 and 8, it is possible to notice the conservation of the epithelial layers, of the cellular nuclei and of the gap-junctions. Moreover, there is a significant reduction of the density of microvilli, though the remaining microvilli are morphologically integer and the deep cytoplasmic cellular membrane is not endangered. Similar results have been obtained with the novel test compositions first, second and third.

Figure 10:
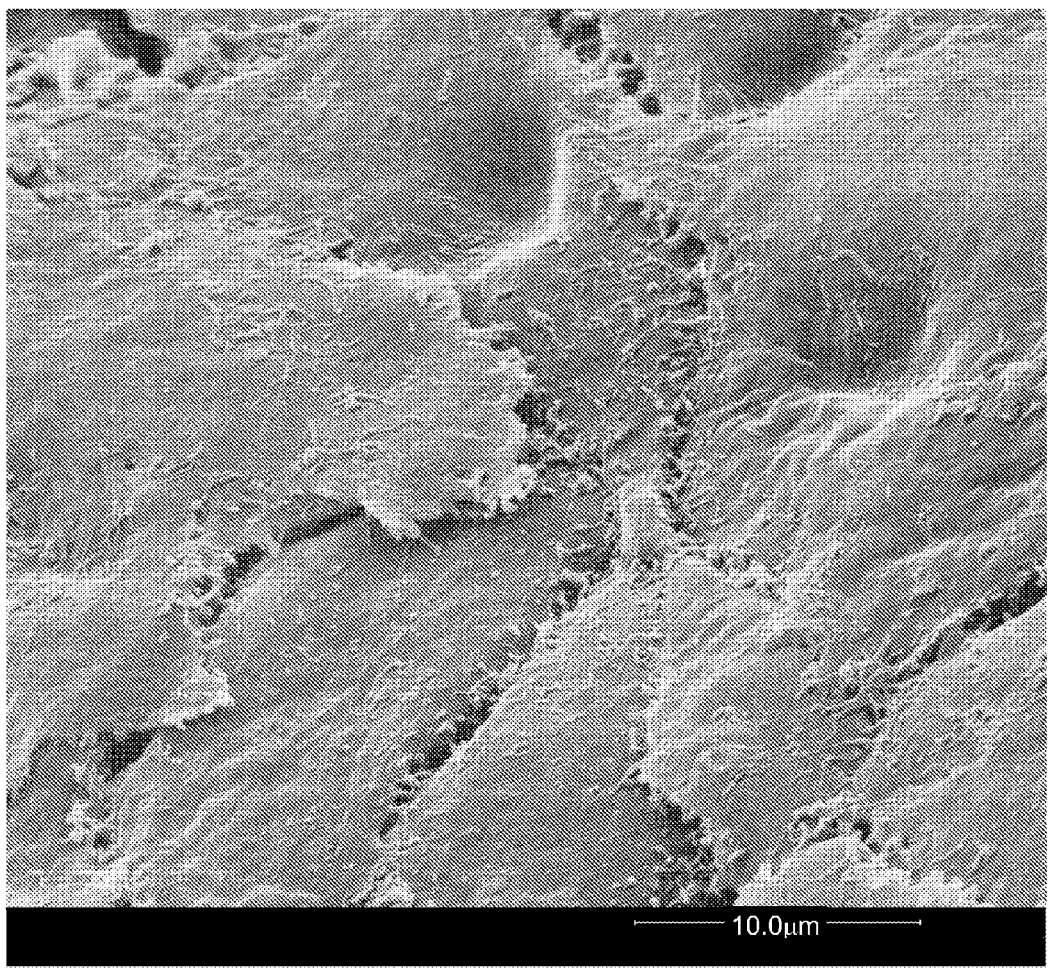
FIG. 10 is a scanning microscopy of a cornea treated with a standard dose of UV-A after having applied a physiological solution in a trans-epithelial fashion.

FIG. 10 is a scanning microscopy of a cornea treated with UV-A at a standard dose using, for sake of comparison, only a physiological solution. The epithelial layers are broken up, numerous cells have lost their cytoplasmic nucleus and almost all gap junctions and microvilli are lost.

The obtained results may be summarized as follows:

1) corneas treated with UV-A with a preliminary incubation with the standard solution of riboflavin-dextran 0.1% or with the composition containing the standard solution+benzalkonium chloride 0.01% according to the standard protocol, undergo to a total loss of all epithelial layers and as a consequence the Bowman's membrane is uncovered (FIG. 8). In practice, using only the standard solution eventually added with benzalkonium chloride, the epithelium is destroyed by the UV-A radiation. This induces to think that the cross-linking treatment carried out without removing the epithelium and using either the standard solution or the composition riboflavin-dextran+benzalkonium chloride would not avoid to patients, after the treatment, the annoying symptoms caused by the surgical removal of the epithelium;

2) corneas treated with a standard dose of UV-A after incubation with compositions comprising riboflavin-dextran and at least a carrier chosen among the ones mentioned above, and in particular after incubation with the fourth novel test composition, have kept their epithelial layers, cellular nuclei and gap-junctions. A significant reduction of the density of microvilli has been noticed, though the remaining microvilli are morphologically integer. The deep cytoplasmic cellular membrane of corneas appears integer;

3) corneas treated with a standard dose of UV-A after incubation with a balanced salt solution (BSS) showed a breaking up of the epithelial layers, the loss of numerous cells of the cytoplasmic nucleus and of almost all gap junctions and microvilli.

Numerous scanning microscopic images have been taken also on the treated corneas with the novel test compositions first, second and third, but they are not reported here because they look substantially identical as those obtained using the fourth novel test composition.

These results induce to infer that at least vitamin E, vitamin Q or coenzyme Q, the tested amino acids such as L-proline, glycine, lysine hydrochloride and L-leucine, help to protect the corneal epithelium and to favor penetration of riboflavin through the corneal epithelium. Among the novel solutions proposed herein, the fourth composition showed the best performances both in terms of penetration time and of preservation of the corneal epithelium.

An explanation of why the proposed substances allow to obtain these outstanding results and of why the substances used in the fourth test composition show a synergistic effect, are not yet completely clear. Without limiting the invention to a theory, the applicants suggest that the reduced damages to the corneal epithelium, that have been detected after treatment with the fourth novel test composition, could be probably due to the cytorepairing action of vitamin E, for example the vitamin E-TPGS, and/or the presence in the solution of at least an essential or conditionally essential amino acid. Probably vitamin E would act on the glutathione oxidase and on peroxide dismutase, that are the enzymes involved in the repairing action of the epithelium, the essential or conditionally essential amino acids would have a cytorepairing action and would probably favor also the cross-linking effect. Moreover, the greater soaking of the tissue by the fourth novel solution probably determines not only an increase of the cross-linking effect, but also a better preservation of the corneal epithelial layers against the dangerous effects of UV-A rays.

With the novel solutions of riboflavin-dextran and at least a carrier (permeation enhancer) chosen among the one proposed herein, it is possible to carry out the cross-linking treatment, for example for the treatment of keratoconus without preventively removing the corneal epithelium. The fact that the corneal epithelium is not removed avoids:

1) ailments due to irritation that typically occur in the first days after the cross-linking treatment according to the standard protocol;
2) the need of applying a therapeutic contact lens after the treatment and, above all,
3) risks of post-surgical corneal infections due to the removal of the corneal epithelium.

Moreover, surgical actions on the cornea are avoided, thus it is possible to execute the treatment in an ambulatory, without needing an operating room and an operating microscope.

The novel solutions could be administered also in the form of eye drops or gel or applied on therapeutic contact lenses before exposition to solar rays, especially during the summer, such to enhance the effect of natural cross-linking due to irradiation of riboflavin with the light of the sun.

The novel solutions could further protect against UV-A the inner structures of the eyeball and thus being used for example for protecting against macula and/or for preventing cataract in persons at risk exposed for many hours to the light of the sun.

Only in order to preserve as long as possible the novel solutions in non single-dose containers, it is possible to add benzalkonium chloride at a concentration comprised between 0.0001% to 0.02%, preferably in a concentration equal to about 0.01%. If the novel solutions should be produced and marketed in single-dose disposable containers, the addition of benzalkonium chloride is not indispensable. The compositions may be further added with preservatives, anti-microbial, anti-mycotics, excipients (only for example, acetic acid) and in general any substance used in the ophthalmic field for making stable and sterile ophthalmic solutions and/or for favoring their assimilation.

As previously stated, the applicants believe that the good performances of the composition obtained by adding to riboflavin at least a substance chosen among vitamin Q, L-proline, glycine, lysine hydrochloride, L-leucine are partially due to the fact that the last substances are essential or conditionally essential amino acids, that would have a cytorepairing function through an increase of the metalloproteinase MMP9. This induce to infer that it may be possible to obtain similar results to those obtained for the novel test compositions first, second, third and fourth by adding to a riboflavin solution, for example the standard riboflavin-dextran solution, at least a substance adapted to increase the metalloproteinase MMP9, likely in a concentration comprised between 0.00001% and 0.5%.

Among the above substances adapted to increase the metalloproteinase MMP9, it is worth mentioning genistein (5,7-Dihydroxy-3-(4-hydroxyphenyl)chromen-4-one), phytoestrogens, cytokines and the so-called NSAID (nonsteroidal anti-inflammatory drugs). Among the NSAID adapted to be used for preparing a riboflavin ophthalmic solution, it is worth mentioning: acetylsalicylic acid (2-acetoxybenzoic acid), flufenamic acid (2-{[3-(Trifluoromethyl)phenyl]amino}benzoic acid), meclofenamic acid (2-[(2,6-dichloro-3-methylphenyl)amino]benzoic acid), mefenamic acid (2-(2,3-dimethylphenyl)aminobenzoic acid), niflumic acid (2-{[3-(trifluoromethyl)phenyl]amino}nicotinic acid), tolfenamic acid (2-[(3-chloro-2-methylphenyl)amino]benzoic acid), benorilate (4-(acetylamino)phenyl 2-(acetyloxy) benzoate), carprofen ((RS)-2-(6-chloro-9H-carbazol-2-yl) propanoic acid), celecoxib (4-[5-(4-methylphenyl)-3-(trifluoromethyl)pyrazol-1-yl]benzenesulfonamide), cinnoxicam (Piroxicam cinnamate or [9-methyl-10,10-dioxo-8-(pyridin-2-ylcarbamoyl)-10$1^{6}$-thia-9-azabic yclo [4.4.0]deca-1,3,5,7-tetraen-7-yl] (E)-3-phenylprop-2-enoate; piroxicam cinnamate), diflunisal (2',4'-difluoro-4-hydroxybiphenyl-3-carboxylic acid), diclofenac (2-[2-[(2,6-dichlorophenyl)amino]phenyl]acetic acid), droxicam (2H, 5H-1,3-Oxazino(5,6-c)(1,2)benzothiazine-2,4(3H)-dione, 5-methyl-3-(2-pyridinyl)-, 6,6-dioxide) etodolac ((RS)-2-(1, 8-Diethyl-4,9-dihydro-3H-pyrano [3,4-b]indol-1-yl)acetic acid), etoricoxib (5-chloro-6'-methyl-3-[4-(methylsulfonyl) phenyl]-2,3'-bipyridine), fenoprofen (2-(3-phenoxyphenyl) propanoic acid), flurbiprofen ((RS)-2-(2-fluorobiphenyl-4-yl)propanoic acid), ibufenac (4-isobutylphenyl acetic acid), ibuprofen ((RS)-2-(4-(2-methylpropyl)phenyl)propanoic acid), indomethacin (2-{1-[(4-chlorophenyl)carbonyl]-5-methoxy-2-methyl-1H-indol-3-yl}acetic acid), ketoprofen ((RS)-2-(3-benzoylphenyl)propanoic acid), ketorolac ((±)-5-benzoyl-2,3-dihydro-1H-pyrrolizine-1-carboxylic acid, 2-amino-2-(hydroxymethyl)-1,3-propanediol), lornoxicam ((3E)-6-chloro-3-[hydroxy(pyridin-2-ylamino)methylene]-2-methyl-2,3-dihydro-4H-thieno[2,3-e][1,2]thiazin-4-one 1,1-dioxide), lumiracoxib ({2-[(2-chloro-6-fluorophenyl) amino]-5-methylphenyl}acetic acid), meloxicam (4-hydroxy-2-methyl-N-(5-methyl-2-thiazolyl)-2H-1,2-benzothiazine-3-carboxamide-1,1-dioxide), metamizole (Sodium [(2, 3-dihydro-1,5-dimethyl-3-oxo-2-phenyl-1H-pyrazol-4-yl) methylamino] methanesulfonate), naproxen ((+)-(S)-2-(6-methoxynaphthalen-2-yl)propanoic acid), nimesulide (N-(4-Nitro-2-phenoxyphenyl)methanesulfonamide), oxaprozin (3-(4,5-diphenyl-1,3-oxazol-2-yl)propanoic acid) parecoxib (N-{[4-(5-methyl-3-phenylisoxazol-4-yl)phenyl] sulfonyl}propanamide), piroxicam ((8E)-8-[hydroxy-(pyridin-2-ylamino)methylidene]-9-methyl-10,10-dioxo-10$\lambda^{6}$-thia-9-azabicyclo[4.4.0]deca-1,3,5-trien-7-one), rofecoxib (4-(4-methylsulfonylphenyl)-3-phenyl-5H-furan-2-one), sulindac ({(1Z)-5-fluoro-2-methyl-1-[4-(methylsulfinyl)

benzylidene]-1H-indene-3-yl}acetic acid), sudoxicam (4-hydroxy-2-methyl-N(2)-thiazolyl-2H-1,2-benzothiazine-3-carboxamide 1,1-dioxide), tenoxicam ((3E)-3-[hydroxy(pyridin-2-ylamino)methylene]-2-methyl-2,3-dihydro-4H-thieno[2,3-e] [1,2]thiazin-4-one 1,1-dioxide), valdecoxib (4-(5-methyl-3-phenylisoxazol-4-yl)benzenesulfonamide).

Moreover, the applicants consider possible to obtain similar results to those of the novel test compositions first, second, third and fourth by adding, to a riboflavin solution, for example to a solution of riboflavin-dextran, at least an essential or conditionally essential amino acid.

Among the potentially useful substances, the most promising one seems to be L-arginine. It may be mixed with a riboflavin solution, for example the standard riboflavin-dextran solution, and eventually in addition to one or more of the substances mentioned above for obtaining novel solutions. Even if not all these substances have been tested yet, it seems reasonable to the applicants to consider that all essential or conditionally essential amino acids may be validly used for facilitating the penetration of riboflavin through the corneal epithelium, in this way protecting the cornea against UV-A rays and against the solar rays absorbed by riboflavin. In particular, is seems reasonable to consider L-arginine a valid carrier like the substances proposed above because it seems reasonable to presume that L-arginine, that is an amino acid precursor of the nitrogen oxide, may deliver nitrogen oxide (NO) at peripheral levels. The use of nitrogen oxide (NO) for treating patients affected by keratoconus by topical application on the corneal epithelium of a substance in which NO is dissolved, is hindered by the poor solubility of NO.

It is yet to be experimentally tested how much L-arginine and the other essential amino acids protect microvilli of the epithelium against UV-A rays used in the cross-linking treatment. If the other essential or conditionally essential amino acids and in particular L-arginine will prove to be useful, as expected, for realizing ophthalmic solutions that allow a trans-epithelial cross-linking treatment while preserving the corneal epithelium, as the applicants consider reasonable, they will be added to a riboflavin solution, for example a standard riboflavin-dextran solution, with a concentration comprised between 0.00001% and 0.5%.

According to a more preferred embodiment, the concentration of L-arginine or of another essential or conditionally essential amino acid ranges between 0.001% and 0.4%. According to a yet more preferred embodiment, the concentration ranges between 0.005% and 0.3%.

According to a yet more preferred embodiment, the concentration ranges between 0.01% and 0.2%. According to a yet more preferred embodiment, the concentration of L-arginine or of another essential or conditionally essential amino acid is about 0.1%.

As an option, it is possible to add L-arginine and/or any other essential or conditionally essential amino acid to any one of the proposed novel solutions.

The dosage of the novel ophthalmic solutions depends on the diagnosed pathology and on its seriousness. Indicatively, it is considered that the dosage may range between one eye drop per day up to a maximum of one eye drop per hour.

The claims as filed are integral part of this description and are herein incorporated by reference. The whole disclosure of the priority Italian patent applications VA2009A000052 and VA2010A000044 in the name of the same applicants is herein incorporated by reference.

REFERENCES

1 Seiler T., Spoerl E., Huhle M., Kamouna A. Conservative therapy of keratoconus by enhancement of collagen cross-links. Invest Ophthalmol. Vis. Sci. 1996; 37:S1017.

2. Seiler T., Quurke A W. Iatrogenic keratectasia after LASIK in a case of forme fruste keratoconus. J Cat Refract Surg. 1998; 24:1007-1009.

3 Spoerl E., Huhle M., Seiler T. "Induction of cross-links in corneal tissue", Exp Eye Res. 1998; 66:97-103.

4 Mazzotta C., Traversi C., Baiocchi S., Sergio P., Caporossi T., Caporossi A. "Conservative treatment of keratoconus by riboflavin-uva-induced cross-linking of corneal collagen: qualitative investigation" Eur J Ophthalmol. 2006; 16:530-5.

5 Caporossi A., Baiocchi S., Mazzotta C., Traversi C., Caporossi T. "Parasurgical therapy for keratoconus by riboflavin-ultraviolet type A rays induced cross-linking of corneal collagen: preliminary refractive results in an Italian study" J Cataract Refract Surg. 2006; 32:837-45.

6 Spoerl E., Seiler T. "Techniques for stiffening the cornea" J Refract Surg. 1999; 15:711-713.

7 Hagele G., Boxer Wachler B S. "Corneal Collagen Crosslinking with Riboflavin (C3-R) for corneal stabilization" Presented at the International Congress of Corneal Cross Linking (CCL). Dec. 9-10, 2005. Zurich, Switzerland.

8 Pinelli, R. "C3-Riboflavin for the treatment of keratoconus" J Cataract & Refractive Surgery Today Europe. 2006; 1:49-50.

9 Pinelli R. "Eyeword", 2007; 5:34-40.

10 Linda J. Müller, Elisabeth Pels, Gijs F. J. M. Vrensen: "The specific architecture of the anterior stroma accounts for maintenance of corneal curvature". Br J Ophthalmol 2001; 85:437-443 (April).

11 Mau T. Trani, Robert N. Lausch2 and John E. Oakes: "Substance P Differentially Stimulates IL-8 Synthesis in Human Corneal Epithelial Cells" Investigative Ophthalmology and Visual Science. 2000; 41:3871-3877.

12 L. J. Muller, L. Pels and G F. Vrensen: "Novel aspects of the ultrastructural organization of human corneal keratocytes" Investigative Ophthalmology & Visual Science, Vol 36, 2557-2567.

13 G. Perrella, P. Brusini, R. Spelat, P. Hossain, A. Hopkinson, H. S. Dua: "Expression of haematopoietic stem cell markers, CD133 and CD34 on human corneal keratocytes" British Journal of Ophthalmology 2007; 91:94-99.

14 Tadashi Senoo, and Nancy C. Joyce: "Cell Cycle Kinetics in Corneal Endothelium from Old and Young Donors" Investigative Ophthalmology and Visual Science. 2000; 41:660-667.

15 L. J. Muller, L. Pels and G F. Vrensen: "Ultrastructural organization of human corneal nerves" Investigative Ophthalmology & Visual Science, Vol 37, 476-488.

16 Italian patent application No. MI2007A002162, 14 Nov. 2007, R. Pinelli, "Collirio per it trattamento del cheratocono con tecnica cross-linking trans-epiteliale".

17 R. Pinelli, A. J. Kannellopoulos, B. S. B. Wachler, E. Spoerl, A. Ertan, S. L. Trokel, "C3-Riboflavin treatments: Where did we come from? Where are we now?", Cataract & Refractive Surgery Today Europe, Summer 2007.

18 Ashim K. Mitra, "Ophthalmic Drug Delivery Systems", Second Edition: Revised And Expanded, Marcell Dekker Inc., NY, 2003.

The invention claimed is:

1. A method for treating keratoconus in an eyeball of a subject in need thereof, the method comprising:
applying an ophthalmic solution to the corneal epithelium of the eyeball of the subject, wherein the ophthalmic solution comprises riboflavin and D-alfa-tocopheryl polyethylene-glycol 1000 succinate (TPGS), wherein the riboflavin concentration of the ophthalmic solution is at least about 0.1% and the TPGS concentration of the ophthalmic solution is at least about 10 mg % ml, and administering UV-A rays to the eyeball of the subject, that has been treated with the ophthalmic solution, to induce collagen cross-linking in the cornea of the eyeball; and wherein the eyeball of the subject has an intact corneal epithelium.

2. The method of claim 1, wherein the ophthalmic solution further comprises a compound selected from the group consisting of L-proline, glycine, lysine hydrochloride, L-leucine and L-arginine.

3. The method of claim 1, wherein the ophthalmic solution comprises a riboflavin-dextran solution, and the TPGS ranges in concentration from 10 mg % to 2000 mg % ml, and the ophthalmic solution further comprises at least one of the following compounds:
  (a) L-proline at a concentration in the range from 0.0001 mg % ml to 2000 mg % ml;
  (b) glycine at a concentration in the range from 0.0001 mg % ml to 2000 mg % ml;
  (c) lysine hydrochloride at a concentration in the range from 0.0001 mg % ml to 2000 mg % ml;
  (d) L-leucine at a concentration in the range from 0.0001 mg % ml to 2000 mg % ml; and
  (e) L-arginine in the range from 0.00001% to 0.5%; and
wherein the riboflavin-dextran solution comprises 0.5% riboflavin.

4. The method of claim 1, wherein the ophthalmic solution comprises a standard riboflavin-dextran solution, and the TPGS concentration is about 500 mg % ml; and the ophthalmic solution optionally further comprises at least one of the following compounds:
  (a) L-proline at a concentration of about 0.1 mg % ml;
  (b) glycine at a concentration of about 0.1 mg % ml;
  (c) lysine hydrochloride at a concentration of about 0.05 mg % ml;
  (d) L-leucine at a concentration of about 0.08 mg % ml;
  (e) L-arginine at a concentration of about 0.1%; and
wherein the standard riboflavin-dextran solution comprises 0.1% riboflavin.

5. The method of claim 1, wherein the ophthalmic solution is in the form of eye drops, ophthalmic gel, or in a form adapted to be applied on therapeutic contact lenses.

6. The method of claim 1, wherein the ophthalmic solution further comprises a permeation enhancer.

7. The method of claim 1, wherein the ophthalmic solution is administered to the cornea for an amount of time sufficient to allow permeation of the corneal stroma.

8. The method of claim 1, which further comprises re-administering the ophthalmic solution to the treated eyeball of the subject and re-administering UV-A rays to the treated eyeball of the subject.

9. The method of claim 1, wherein the TPGS content of the ophthalmic solution ranges in concentration from 10 mg % ml to 1000 mg % ml.

10. The method of claim 1, wherein the ophthalmic solution further comprises dextran.

11. The method of claim 10, wherein the riboflavin content of the ophthalmic solution is 0.1%.

12. The method of claim 1, wherein the TPGS concentration of the ophthalmic solution is 500 mg % ml.

13. The method of claim 1, wherein the ophthalmic solution is administered to the cornea for an amount of time sufficient to allow permeation of the cornea.

* * * * *